US010738083B2

(12) United States Patent
Van Dongen et al.

(10) Patent No.: US 10,738,083 B2
(45) Date of Patent: Aug. 11, 2020

(54) INFLUENZA VIRUS NEUTRALIZING PEPTIDOMIMETIC COMPOUNDS

(71) Applicant: Janssen Vaccines & Prevention B.V., Leiden (NL)

(72) Inventors: Maria Van Dongen, Hilversum (NL); Christophe Francis Robert Nestor Buyck, Hamme (BE); Wim Bert Griet Schepens, Sint-Katelijne-Waver (BE); Jaroslaw Juraszek, Amsterdam (NL); Bart Rudolf Romanie Kesteleyn, Berlare (BE); Pierre Jean-Marie Bernard Raboisson, Rosieres (BE); Boerries Brandenburg, Utrecht (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 246 days.

(21) Appl. No.: 15/572,976

(22) PCT Filed: May 10, 2016

(86) PCT No.: PCT/EP2016/060438
§ 371 (c)(1),
(2) Date: Nov. 9, 2017

(87) PCT Pub. No.: WO2016/180826
PCT Pub. Date: Nov. 17, 2016

(65) Prior Publication Data

US 2018/0118788 A1 May 3, 2018

Related U.S. Application Data

(60) Provisional application No. 62/159,833, filed on May 11, 2015.

(30) Foreign Application Priority Data

Jun. 22, 2015 (EP) .................................... 15173078

(51) Int. Cl.

| | |
|---|---|
| ***A61K 38/08*** | (2019.01) |
| ***A61K 38/12*** | (2006.01) |
| ***C07K 7/06*** | (2006.01) |
| ***C07K 7/56*** | (2006.01) |
| ***G01N 33/569*** | (2006.01) |
| ***A61P 31/16*** | (2006.01) |
| *A61K 38/00* | (2006.01) |

(52) U.S. Cl.
CPC ................ *C07K 7/56* (2013.01); *A61K 38/08* (2013.01); *A61K 38/12* (2013.01); *A61P 31/16* (2018.01); *C07K 7/06* (2013.01); *G01N 33/56983* (2013.01); *A61K 38/00* (2013.01); *C12N 2760/16111* (2013.01)

(58) Field of Classification Search
CPC .......... A61K 38/08; A61K 38/12; C07K 7/06; C07K 7/56
See application file for complete search history.

(56) References Cited

U.S. PATENT DOCUMENTS

| | | | | |
|---|---|---|---|---|
| 8,877,200 B2 * | 11/2014 | Shriver | A61K 39/145 424/159.1 |
| 2011/0274702 A1 | 11/2011 | Lanzavecchia | |
| 2013/0302348 A1 * | 11/2013 | Raguram | C07K 16/1018 424/159.1 |

FOREIGN PATENT DOCUMENTS

| | | |
|---|---|---|
| WO | 2008/028946 A2 | 3/2008 |
| WO | 2013/007770 A1 | 1/2013 |

OTHER PUBLICATIONS

Int'l Search Report dated Jul. 11, 2016 in Int'l Application No. PCT/EP2016/060438.
Written Opinion dated Jul. 11, 2016 in Int'l Application No. PCT/EP2016/060438.
Hoffmann et al, "A new class of synthetic anti-lipopolysaccharide peptides inhibits influenza A virus replication by blocking cellular attachment," Antiviral Research, vol. 104, No. 30, pp. 23-33 (Jan. 30, 2014).
Rajik et al, "A novel peptide inhibits the influenza virus replication by preventing the viral attachment to the host cells," International Journal of Biological Sciences, vol. 5, No. 6, pp. 543-548 (Aug. 8, 2009).
Corti et al, "A Neutralizing Antibody Selected from Plasma Cells That Bind to Group 1 and Group 2 Influenza A Hemagglutinins," Science, vol. 333, pp. 850-856 (Aug. 12, 2011).

* cited by examiner

*Primary Examiner* — Jeffrey E. Russel
(74) *Attorney, Agent, or Firm* — Ice Miller LLP

(57) ABSTRACT

The present invention relates to novel peptidomimetic compounds that are capable of binding to and/or neutralizing influenza viruses, in particular influenza A viruses of phylogenetic group 1, and to pharmaceutical compositions comprising such compounds. The invention also relates to the use of the peptidomimetic compounds in the diagnosis, prophylaxis and/or treatment of influenza virus infections.

32 Claims, 1 Drawing Sheet

Specification includes a Sequence Listing.

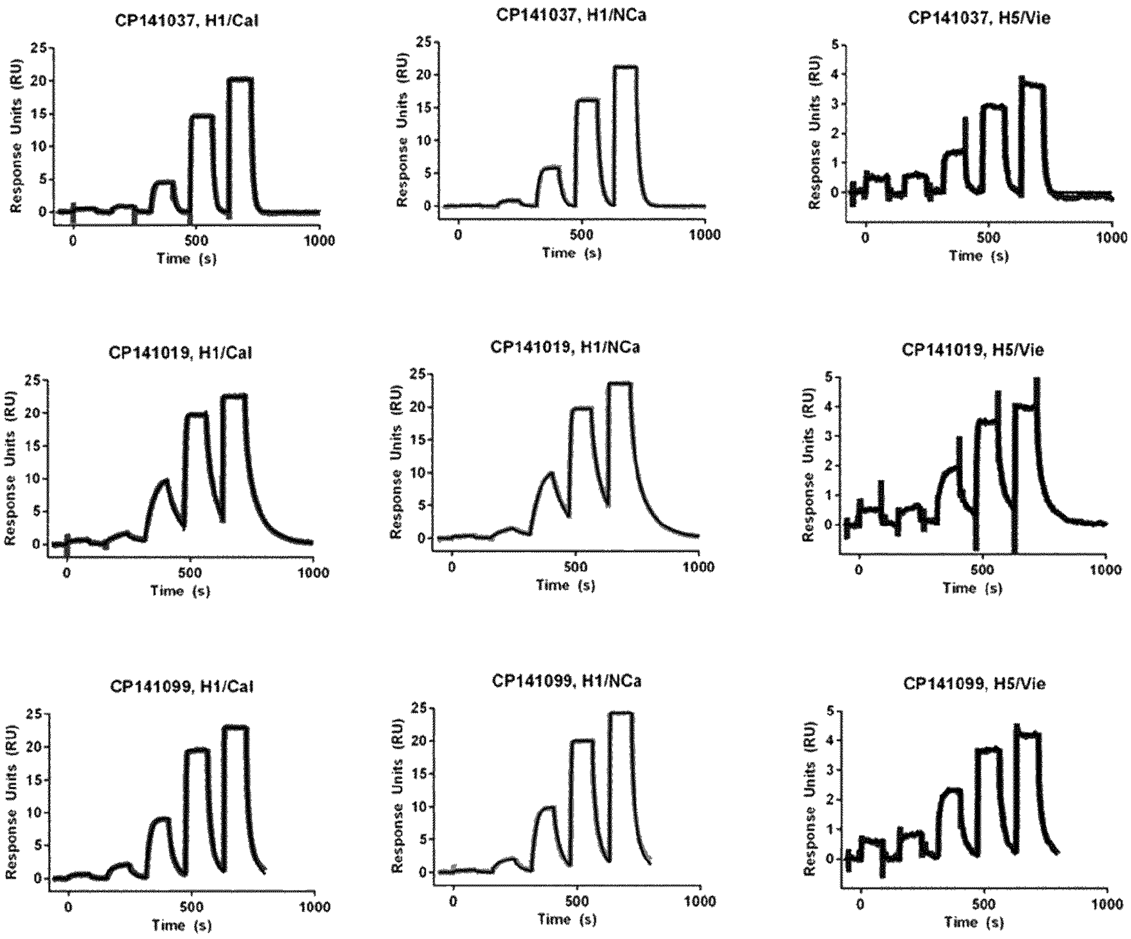
CP141037, H1/Cal
CP141037, H1/NCa
CP141037, H5/Vie
CP141019, H1/Cal
CP141019, H1/NCa
CP141019, H5/Vie
CP141099, H1/Cal
CP141099, H1/NCa
CP141099, H5/Vie
Response Units (RU)
Time (s)
0
500
1000
0
5
10
15
20
25
1
2
3
4

INFLUENZA VIRUS NEUTRALIZING PEPTIDOMIMETIC COMPOUNDS

CROSS REFERENCE TO RELATED APPLICATIONS

This application is a section 371 of International Application No. PCT/EP2016/060438, filed on May 10, 2016, which was published in the English Language on Nov. 17, 2016, under International Publication No. WO2016/180826, which claims priority to U.S. Provisional Application No. 62/159,833, filed on May 11, 2015 and European Patent Application No. 15173078.5, filed on Jun. 22, 2015.

REFERENCE TO SEQUENCE LISTING SUBMITTED ELECTRONICALLY

This application contains a sequence listing, which is submitted electronically via EFS-Web as an ASCII formatted sequence listing with a file name "688097-396US Sequence Listing" and a creation date of Nov. 1, 2017, and having a size of 6 kb. The sequence listing submitted via EFS-Web is part of the specification and is herein incorporated by reference in its entirety.

FIELD OF THE INVENTION

The present invention relates to the field of medicine. The present invention relates to novel peptidomimetic compounds that are capable of binding to and/or neutralizing influenza viruses, in particular influenza A viruses of phylogenetic group 1, and to pharmaceutical compositions comprising such compounds. The invention also relates to the use of the peptidomimetic compounds in the diagnosis, prophylaxis and/or treatment of influenza virus infections.

BACKGROUND

Seasonal influenza A is a major public health problem, killing more than 250,000 worldwide each year, while creating an economic burden for millions. Pandemic influenza, which occurs when a new virus emerges and infects people globally that have little or no immunity, represents even a greater threat to human health; for example, the 1918 "Spanish Flu" pandemic caused an estimated 50 million deaths. Of continuing concern is highly pathogenic avian influenza (HPAI) which has demonstrated mortality rates of greater than 50% in infected humans. H5 as well as H7 influenza viruses are endemic in poultry in certain parts of the world. These viruses currently do not appear to be able to transmit readily from person to person, but recent data for avian H5 indicate that only a few amino acid changes are sufficient to enable this virus to spread through aerosol transmission in a mammalian in vivo model system.

Antibodies capable of broadly neutralizing influenza A and/or B viruses have recently been described, such as CR9114 (as disclosed in WO2013/007770), CR6261 (disclosed in WO2008/028946), FI6 (described in Corti et al., Science 333, 850-856 (2011)). These antibodies have been shown to interact with a large variety of hemagglutinin proteins and to neutralize a broad spectrum of influenza strains. As a result of their potency and breadth, such antibodies are now being developed for therapeutic treatment of severely ill patients and prophylactic applications for people belonging to high risk groups. The relative high costs of goods and their parenteral administration, however, are expected to limit the use of monoclonal antibodies in larger populations.

Other currently available agents to prevent and/or treat influenza infection are also associated with severe limitations. Anti-viral drugs such as the neuraminidase inhibitors oseltamivir and zanamivir and the M2 inhibitors amantadine and rimantadine have limited efficacy if administered late in infection and widespread use is likely to result in the emergence of resistant viral strains. Furthermore the use of oseltamivir in adults is associated with adverse effects, such as nausea, vomiting, psychiatric effects and renal events.

Furthermore, the efficacy of influenza vaccines has been shown to be suboptimal for high-risk patients (elderly) and the permanent antigenic changes of the circulating influenza viruses requires annual adaptation of the influenza vaccine formulation to ensure the closest possible match between the influenza vaccine strains and the circulating influenza strains.

The discovery of novel influenza antivirals acting on hemagglutinin (HA) as an alternative strategy to prevent and/or treat influenza infection is also hampered by the large sequence variability of this protein. Hemagglutinin ligands described so far therefore only show activity against a limited number of closely related influenza strains.

In view of the severity of respiratory illness caused by influenza A viruses, as well has the high economic impact of the seasonal epidemics, and the continuing risk for pandemics, there is an ongoing need for new effective inhibitors with broad activity against influenza A viruses and which can be used as medicaments for prevention or treatment of influenza infection.

SUMMARY OF THE INVENTION

The present invention provides novel peptidomimetic compounds that are capable of specifically binding to hemagglutinin (HA) of at least two influenza A virus strains comprising HA of different subtypes from phylogenetic group 1. In certain embodiments, the compounds are capable of specifically binding to at least one influenza virus strain comprising HA of the H1 subtype, such as an H1N1 influenza virus strain, and at least one influenza virus strain comprising HA of the H5 subtype, such as an H5N1 influenza virus strain. At least some of the compounds are capable of neutralizing at least two influenza A virus strains comprising HA of different subtypes from phylogenetic group 1. In certain embodiments, the compounds are capable of specifically neutralizing at least one influenza virus strain comprising HA of the H1 subtype, such as an H1N1 influenza virus strain, and at least one influenza virus strain comprising HA of the H5 subtype, such as an H5N1 influenza virus strain.

In certain embodiments, the compounds have the following sequence:

Cap1-X1-X2-X3-X4-X5-X6-X7-X8-Leu-X9-X10-Cap2 wherein Cap1 is any amino acid sequence comprising from 0-10 residues with a N-terminal blocking group;

X1 is any L or D-amino acid;

X2 is any L-amino acid;

X3 is an aliphatic L-amino acid with a molecular weight below 200 Da;

X4 is any L-amino acid;

X5 is Tyr or a L-tyrosine analog;

X6 is Phe or a L-phenylalanine analog;

X7 is any charged or neutral hydrophilic L-amino acid;
X8 is Trp or a L-tryptophan analog;
X9 is absent or any hydrophilic L-amino acid;
X10 is any L-amino acid; and
Cap2 is any amino acid sequence comprising from 0-10 residues with a C-terminal blocking group.

The invention further provides cyclized peptidomimetic compounds. In certain embodiments, the compounds thus have a sequence selected from:

Cap1-X1-[X2-X3-X4-X5-X6-X7-X8-Leu-X9-X10]-Cap2

Cap1-X1-X2-X3-[X4-X5-X6-X7-X8-Leu-X9-X10]-Cap2 and

Cap1-X1-[X2-X3-X4-X5-X6-X7-X8-Leu-X9-X10]-Cap2 wherein Cap1 is any amino acid sequence comprising from 0-10 residues with a N-terminal blocking group;
X1 is any L or D-amino acid;
X2 is any L-amino acid;
X3 is an aliphatic L-amino acid with a molecular weight below 200 Da;
X4 is any L-amino acid;
X5 is Tyr or a L-tyrosine analog;
X6 is Phe or a L-phenylalanine analog;
X7 is any charged or neutral hydrophilic L-amino acid;
X8 is Trp or L-tryptophan analog;
X9 is absent or any hydrophilic L-amino acid;
X10 is any L-amino acid; and
Cap2 is any amino acid sequence comprising from 0-10 residues with a C-terminal blocking group.

In yet another aspect, the invention provides multimeric, in particular dimeric peptidomimetic compounds. In certain embodiments, the compounds thus have a sequence:

Cap1-X1-[X2-X3-X4-X5-X6-X7-X8-Leu-X9-X10]-Cap2

Cap1-X1-[X2-X3-X4-X5-X6-X7-X8-Leu-X9-X10]-Cap2 wherein Cap1 is any amino acid sequence comprising from 0-10 residues with a N-terminal blocking group;
X1 is any L or D-amino acid;
X2 is any L-amino acid;
X3 is an aliphatic L-amino acid with a molecular weight below 200 Da;
X4 is any L-amino acid;
X5 is Tyr or a L-tyrosine analog;
X6 is Phe or a L-phenylalanine analog;
X7 is any charged or neutral hydrophilic L-amino acid;
X8 is Trp or a L-tryptophan analog;
X9 is absent or any hydrophilic L-amino acid;
X10 is any L-amino acid; and
Cap2 is any amino acid sequence comprising from 0-10 residues with a C-terminal blocking group.

The invention furthermore provides pharmaceutical compositions comprising at least one compound as described herein and a pharmaceutically acceptable carrier or diluent.

The invention also relates to compounds as described herein for use in the diagnosis, prevention and/or treatment of influenza.

BRIEF DESCRIPTION OF THE FIGURES

FIG. 1: Binding curves of CP141037, CP141019 and CP141099 for HA derived from three influenza strains (A/California/07/09 (left), A/New Caledonia/20/99 (middle), A/Vietnam/1194/04 (right)) are presented. Response units (RU) are plotted as a function of time upon injection of increasing amount of compound. Curves are the trace obtained from SPR experiments, and overlaid thin black lines are the best fits of the 1:1 Langmuir binding model to the data.

DETAILED DESCRIPTION OF THE INVENTION

In the research that led to the present invention novel peptidomimetic compounds were developed guided by structural data of HA complexes with inter alia the monoclonal antibodies CR6261, CR9114 and FI6. Peptidomimetic compounds (also referred to as 'peptidomimetics') typically are small protein-like molecules designed to mimic natural peptides or proteins. The peptidomimetics preferably have the ability to bind to their natural targets in the same way as the natural peptides do and hence should have the same biological effect. It is further possible to design these molecules in such a way that they show the same biological effect as the natural peptide but with enhanced properties, like a higher proteolytic stability, bioavailability, selectivity and/or potency.

The peptidomimetic compounds of the present invention have been shown to have a competitive binding activity at least towards HA of the H1 subtype, such as the H1N1 influenza virus strains A/California/07/2009 and A/New Caledonia/20/1999, and towards HA of the H5 subtype, such as the H5N1 influenza strain A/Vietnam/1203/2004. At least some of the compounds of the invention also have been shown to have neutralizing activity against at least two different influenza A virus strains each comprising HA of a different HA subtype from phylogenetic group 1, such as against influenza viruses comprising HA of the H1 subtype, such as the H1N1 influenza virus strains A/California/07/2009 and A/New Caledonia/20/1999, and against influenza virus comprising HA of the H5 subtype, such as the H5N1 influenza strain A/Vietnam/1203/2004. The compounds of the invention offer several advantages relative to anti-influenza antibodies, including the small size (1.5 kDa), low cost chemical production, simple engineering into multimeric formats, and high stability with the potential to support non-injectable routes of administration.

In a first aspect, the present invention thus provides novel peptidomimetic compounds having the following sequence:

Cap1-X1-X2-X3-X4-X5-X6-X7-X8-Leu-X9-X10-Cap2 wherein Cap1 is an amino acid sequence comprising from 0-10 residues with a N-terminal blocking group;
X1 is any L or D-amino acid;
X2 is any L-amino acid;
X3 is an aliphatic L-amino acid with a molecular weight below 200 Da;
X4 is any L-amino acid;
X5 is Tyr or a L-tyrosine analog;
X6 is Phe or a L-phenylalanine analog;

X7 is any charged or neutral hydrophilic L-amino acid;

X8 is Trp or a L-tryptophan analog;

X9 is absent or any hydrophilic L-amino acid;

X10 is any L-amino acid; and

Cap2 is an amino acid sequence comprising from 0-10 residues with a C-terminal blocking group.

As indicated above, the compounds of the invention are capable of specifically binding to hemagglutinin (HA) of at least two influenza A virus strains comprising HA of different subtypes from phylogenetic group 1. In certain embodiments, the compounds are capable of specifically binding to at least one influenza virus strain comprising HA of the H1 subtype, such as an H1N1 influenza virus strain, and at least one influenza virus strain comprising HA of the H5 subtype, such as an H5N1 influenza virus strain. In certain embodiments, the compounds are capable of specifically binding to at least one influenza virus strain comprising HA of the H1 subtype, such as an H1N1 influenza virus strain, and at least one influenza virus strain comprising HA of the H5 subtype, such as an H5N1 influenza virus strain.

In certain embodiments, the compounds are capable of specifically binding to at least two, preferably to at least three, more preferably to at least four different influenza virus strains comprising HA of the H1 subtype. In certain embodiments, the compounds are capable of specifically binding to at least two, preferably to at least three, more preferably to at least four different influenza virus strains comprising HA of the H5 subtype. In certain embodiments, the compounds are capable of neutralizing at least two, preferably at least three, more preferably at least four different influenza virus strains comprising HA of the H1 subtype In certain embodiments, the compounds are capable of binding to at least one influenza virus comprising HA of another subtype from phylogenetic group 1, such as the H2 and/or H9 subtype.

The term "specifically binding" as used herein refers to compounds that bind to an epitope of the protein of interest, i.e. HA, but which do not substantially recognize and bind other molecules in a sample containing a mixture of antigenic biological molecules. Typically, the compounds of the invention bind to HA of an influenza A virus of group 1 with an affinity constant (Kd-value) below 10 μM, preferably below 1 μM, more preferably below 0.1 μM, even more preferably below 10 nM, even more preferably below 1 nM.

As used throughout the description, the term "influenza virus subtype" in relation to influenza A viruses refers to influenza A virus strains that are characterized by various combinations of the hemagglutinin (H) and neuraminidase (N) viral surface proteins. Influenza A virus subtypes may be referred to by their H number, such as for example "influenza virus comprising HA of the H1 or H5 subtype", or "H1 influenza virus", "H5 influenza virus", or by a combination of an H number and an N number, such as for example "influenza virus subtype "H1N1" or "H5N1". The term influenza virus "subtype" specifically includes all individual influenza virus "strains" within such subtype, which usually are different as a result of mutations in hemagglutinin and/or neuraminidase, and show different pathogenic profiles, and include natural isolates as well as man-made mutants or reassortants and the like. Such strains may also be referred to as various "isolates" of a viral subtype. Accordingly, as used herein, the terms "strains" and "isolates" may be used interchangeably. The influenza A virus subtypes can further be classified by reference to their phylogenetic group. Phylogenetic analysis thus has demonstrated a subdivision of influenza hemagglutinins into two main groups: inter alia the H1, H2, H5 and H9 subtypes in phylogenetic group 1 ("group 1" influenza viruses) and inter alia the H3, H4, H7 and H10 subtypes in phylogenetic group 2 ("group 2" influenza viruses).

An amino acid according to the invention can be any of the twenty naturally occurring (or 'standard' amino acids) or variants thereof, such as e.g. D-amino acids (the D-enantiomers of amino acids with a chiral center), or any variants that are not naturally found in proteins. Table 5 shows the abbreviations and properties of the standard amino acids.

In certain embodiments of the invention, X3 is an aliphatic L-amino acid with a molecular weight below 200 Da with a linear or C-gamma-branched side chain; X5 is Tyr or a L-tyrosine analog having a hydrogen bond donor and/or acceptor replacing the hydroxyl group of tyrosine; X6 is Phe or a L-phenylalanine analog with one or more substituents selected from the group consisting of hydrogen, halogen, a C1-C4 alkyl on the ortho and/or meta positions of the phenyl ring, halogen at the para position of the phenyl ring, L-3-naphtalen-1-yl-alanine, and L-3-naphtalen-2-yl-alanine; and X8 is Trp or a L-tryptophan analog with a halogen substituent at C5, C6 and/or C7, and/or a small aliphatic substituent on C2 of the indole ring.

In a further aspect, the present invention provides cyclic compounds. Cyclization reduces the flexibility of the compounds, and results in higher affinity and potency, as well as in enhanced properties, like a higher proteolytic stability, bioavailability and/or selectivity. Thus, in certain embodiments, the compounds as described herein are cyclized. In certain embodiments, the compounds are cyclized via a chemical bridge between residues X2 and X10 and/or between residues X4 and X10. In certain embodiments, the compounds are cyclized via the formation of an amide bond comprising residues X2 and X10. In certain embodiments, the compounds are cyclized via the formation of an amide bond comprising residues X4 and X10.

Thus, in certain embodiments, the compounds have a sequence selected from the group consisting of:

Cap1-X1-[X2-X3-X4-X5-X6-X7-X8-Leu-X9-X10]-Cap2

Cap1-X1-X2-X3-[X4-X5-X6-X7-X8-Leu-X9-X10]-Cap2 and

Cap1-X1-[X2-X3-X4-X5-X6-X7-X8-Leu-X9-X10]-Cap2 wherein Cap1 is an amino acid sequence comprising from 0-10 residues with a N-terminal blocking group;

X1 is any L or D-amino acid;

X2 is any L-amino acid;

X3 is an aliphatic L-amino acid with a molecular weight below 200 Da;

X4 is any L-amino acid;

X5 is Tyr or a L-tyrosine analog;

X6 is Phe or a L-phenylalanine analog;

X7 is any charged or neutral hydrophilic L-amino acid;

X8 is Trp or a L-tryptophan analog;

X9 is absent or any hydrophilic L-amino acid;

X10 is any L-amino acid; and

Cap2 is an amino acid sequence comprising from 0-10 residues with a C-terminal blocking group.

In certain embodiments, X2 and/or X4 is any L-amino acid with a functional group that can be used for cyclization, wherein the functional group is 2-5 atoms away from the C-alpha atom of the L-amino acid; and X10 is any L-amino acid with a functional group that can be used for cyclization, wherein the functional group is 2-5 atoms away from the C-alpha atom of the L-amino acid.

In certain embodiments, X2 is Lys or L-ornithine, and X10 is beta-alanine, 3-aminoproprionic acid, 3-amino-2,2-dimethyl-proprionic acid, 4-aminobutanoic acid, 5-aminopentanoic acid, 6-aminoohexanoic acid, or Pro.

In certain embodiments, X2 is Asp or Glu and X10 is Lys or L-ornithine.

In certain embodiments, X4 is Lys or L-ornithine and X10 is beta-alanine, 3-aminoproprionic acid, 3-amino-2,2-dimethyl-proprionic acid, 4-aminobutanoic acid, 5-aminopentanoic acid, 6-aminoohexanoic acid, or Pro.

In certain embodiments, X4 is Asp or Glu, and X10 is Lys or L-ornithine.

In certain embodiments, the compounds are cyclized via a chemical bridge between residues X2 and X10 and X4 and X10.

In certain embodiments, the compounds are cyclized by means of intramolecular cross-linking of free amine groups introduced at residues X2 and X4 and X10 with tris-succinimidyl aminotriacetate (TSAT).

In yet a further aspect, the present invention provides multimeric peptidomimetic compounds, wherein the multimeric compounds comprise two or more compounds as described herein. In certain embodiments, the compounds are dimeric. In certain embodiments, the residue involved in linking the monomers is in the X4 position. Thus, in certain embodiments the compounds are multimerized by intermolecular cross-linking of reactive groups introduced at residue X4. The compounds of the invention may be homodimers (i.e. comprising two similar monomeric compounds) or may be heterodimers.

In certain embodiments, the compounds of the invention have a sequence:

Cap1-X1-[X2-X3-X4-X5-X6-X7-X8-Leu-X9-X10]-Cap2
|
Cap1-X1-[X2-X3-X4-X5-X6-X7-X8-Leu-X9-X10]-Cap2 wherein Cap1, X1 to X10 and Cap2 are as defined above.

In certain embodiments, the compounds are dimerized by intermolecular cross-linking of reactive groups introduced at residue X4, with a linker composed of 2-20 repeating ethylene glycol units.

As define above, in the linear, cyclized and/or multimeric compounds of the present invention, Cap1 and/or Cap2 may be an amino acid sequence comprising from 0 to 10 additional residues. Thus, according to the invention, Cap 1 and/or Cap 2 may be absent, or an amino acid sequence of up to 10 additional residues (natural or unnatural amino acids) may be present at the N-terminal site, and/or up to 10 additional residues (natural or unnatural amino acids) may be present at the C-terminal site of the core sequences as given herein. The C- and/or N-terminal blocking group may be any arbitrary blocking group that is known in the art. N-terminal blocking groups are e.g. acetyl or succinyl. A C-terminal blocking group is for example carboxamide.

In certain embodiments of the invention, Cap1 is acetyl or succinyl.

As defined above, according to the invention, X1 may be any L or D-amino acid. In certain embodiments, X1 is (S)-2-amino-5-phenylpentanoic acid, (2S)-3,3-dimethyl-2-amino-5-phenylpentanoic acid or Arg.

In certain embodiments, X2 is Lys, L-ornithine, Cys, L-homo-cysteine, or Ser.

In certain embodiments, X3 is Leu, L-norleucine, L-cyclopentylalanine, L-cyclobutylalanine, L-cyclopropylalanine, (2S,4S)-2-amino-4-methylhexanoic acid, (2S,4R)-2-amino-4-methylhexanoic acid, (2S,4S)-2-amino-4-methylheptanoic acid, (2S,4R)-2-amino-4-methylheptanoic acid, (S)-2-amino-4-ethylhexanoic acid, or an N-methylated derivative thereof.

In certain embodiments, X4 is Asp, Glu, Arg, Lys, ornithine, cysteine, homocysteine,
N6-(4-carboxybutanoyl)lysine, or N5-(4-carboxybutanoyl)ornithine.

In certain embodiments X5 is Tyr.

In certain embodiments, X6 is Phe, L-2-chlorophenylalanine, L-3-chlorophenylalanine, L-4-chlorophenylalanine, or L-3,4-dichlorophenylalanine.

As defined above, X7 may be any charged or neutral hydrophilic L-amino acid. In certain embodiments, X7 is Glu, Gln, Asp, Asn, Arg or Lys.

In certain embodiments, X8 is Trp or L-2-methyl-tryptophan.

As defined above, according to the invention X9 may be absent or may be any hydrophilic L-amino acid. In certain embodiments, X9 is Ser or Gln.

As defined above, according to the invention X10 may be any L-amino acid. In certain embodiments, X10 is 4-aminobutanoic acid, beta-alanine, ((2R)-3-amino-2-(3-aminopropanoylamino) beta-alanine, Lys, L-ornithine, Cys or homocysteine.

In certain embodiments, Cap2 is absent.

In at least certain embodiments, the compounds are capable of neutralizing at least two influenza A virus strains comprising HA of different subtypes from phylogenetic group 1. In certain embodiments, the compounds are capable of specifically neutralizing at least one influenza virus strain comprising HA of the H1 subtype, such as an H1N1 influenza virus strain, and at least one influenza virus strain comprising HA of the H5 subtype, such as an H5N1 influenza virus strain.

In certain embodiments, the compounds are capable of neutralizing at least two, preferably at least three, more preferably at least four different influenza virus strains comprising HA of the H1 subtype. In certain embodiments, the compounds are capable of neutralizing at least two, preferably at least three, more preferably at least four different influenza virus strains comprising HA of the H5 subtype.

In certain embodiments, the compounds are capable of neutralizing at least one influenza virus comprising HA of another subtype from phylogenetic group 1, such as the H2 and/or H9 subtype. In certain embodiments of the invention, thus cross-neutralizing compounds are provided.

The term "neutralizing" or "neutralization" as used herein in relation to compounds of the invention refers to the ability of a compound to inhibit an influenza virus from replication, in vitro and/or in vivo within a subject, regardless of the mechanism by which neutralization is achieved. In some embodiments, the compounds of the invention neutralize influenza virus through the inhibition of the fusion of viral and cellular membranes following attachment of the virus to the target cell. The term "cross-neutralizing" or "cross-neutralization" as used herein in relation to the compounds of the invention refers to the ability to neutralize influenza virus strains of different subtypes of influenza A. Neutralizing activity can for instance be measured as described herein. Alternative assays measuring neutralizing activity are described in for instance WHO Manual on Animal Influenza Diagnosis and Surveillance, Geneva: World Health Organisation, 2005, version 2002.5. Typically, the compounds of the invention have a neutralizing activity of 1 μM or less, preferably 100 nM or less, more preferably 10 nM or less, as determined in an in vitro virus neutralization assay (VNA), e.g. as described in the Examples.

In certain embodiments of the invention, Cap1 is acetyl; X1 is (S)-2-amino-5-phenylpentanoic acid; X2 is L-ornithine; X3 is leucine; X4 is arginine; X5 is tyrosine; X6 is phenylalanine; X7 is glutamic acid; X8 is tryptophan; X9 is serine; X10 is beta-alanine; and Cap2 is absent, wherein the compound is cyclized via an amide bond between residue X2 and X10 (side chain X2 to tail lactam formation).

In certain embodiments of the invention, Cap1 is acetyl; X1 is (S)-2-amino-5-phenylpentanoic acid; X2 is L-ornithine; X3 is leucine; X4 is glutamic acid; X5 is tyrosine; X6 is L-3,4-dichlorophenylalanine; X7 is glutamic acid; X8 is tryptophan; X9 is serine; X10 is beta-alanine; and Cap2 is absent, wherein the compound is cyclized via an amide bond between X2 and X10 (side chain X2 to tail lactam formation).

In certain embodiments of the invention, Cap1 is acetyl; X1 is (S)-2-amino-5-phenylpentanoic acid; X2 is L-ornithine; X3 is L-cyclopentylalanine; X4 is glutamic acid; X5 is tyrosine; X6 is phenylalanine; X7 is glutamic acid; X8 is tryptophan; X9 is serine; X10 is beta-alanine; and Cap2 is absent, wherein the compound is cyclized via an amide bond between X2 and X10 (side chain X2 to tail lactam formation).

In certain embodiments of the invention, Cap1 is acetyl; X1 is (S)-2-amino-5-phenylpentanoic acid; X2 is L-ornithine; X3 is L-N-methyl-leucine; X4 is glutamic acid; X5 is tyrosine; X6 is phenylalanine; X7 is glutamic acid; X8 is tryptophan; X9 is serine; X10 is beta-alanine; and Cap2 is absent, wherein the compound is cyclized via an amide bond between X2 and X10 (side chain X2 to tail lactam formation).

In certain embodiments of the invention, Cap1 is acetyl; X1 is (S)-2-amino-5-phenylpentanoic acid; X2 is L-ornithine; X3 is leucine; X4 is N6-(4-carboxybutanoyl)lysine; X5 is tyrosine; X6 is phenylalanine; X7 is glutamic acid; X8 is tryptophan; X9 is serine; X10 is beta-alanine; and Cap2 is absent, wherein the compound is cyclized via an amide bond between X2 and X10 (side chain X2 to tail lactam formation).

In certain embodiments of the invention, Cap1 is acetyl; X1 is (S)-2-amino-5-phenylpentanoic acid; X2 is L-ornithine; X3 is leucine; X4 is glutamic acid; X5 is tyrosine; X6 is phenylalanine; X7 is glutamic acid; X8 is tryptophan; X9 is glutamine; X10 is beta-alanine; and Cap2 is absent, wherein the compound is cyclized via an amide bond between X2 and X10 (side chain X2 to tail lactam formation).

In certain embodiments of the invention, Cap1 is acetyl; X1 is (S)-2-amino-5-phenylpentanoic acid; X2 is L-ornithine; X3 is leucine; X4 is N6-(4-carboxybutanoyl)lysine; X5 is tyrosine; X6 is phenylalanine; X7 is glutamic acid; X8 is tryptophan; X9 is serine; X10 is beta-alanine; and Cap2 is absent, wherein the compound is cyclized via intramolecular side-chain of X2 to tail formation and dimerized via a X4 amide linked polyethylene glycol spacer containing 13 ethylene units (PEG13).

In certain embodiments of the invention, Cap1 is acetyl; X1 is (S)-2-amino-5-phenylpentanoic acid; X2 is L-omithine; X3 is leucine; X4 is glutamic acid; X5 is tyrosine; X6 is phenylalanine; X7 is glutamic acid; X8 is tryptophan; X9 is serine, X10 is ((2R)-3-amino-2-(3-aminopropanoylamino) beta-alanine; and Cap2 is absent, wherein the compound is cyclized via an amide bond between X2 and X10 (side chain X2 to tail lactam formation).

In certain embodiments of the invention, Cap1 is acetyl; X1 is (S)-2-Amino-5-phenylpentanoic acid; X2 is L-omithine; X3 is leucine; X4 is L-ornithine; X5 is tyrosine; X6 is phenylalanine; X7 is glutamic acid; X8 is tryptophan; X9 is serine, X10 is L-omithine and Cap2 is carboxamide, wherein the compound is cyclized by TSAT (tris-succinimidyl)aminotriacetate) mediated linkage of X2, X4 and X10.

In certain embodiments, the compound has a sequence selected from the group consisting of:

(SEQ ID NO: 1)

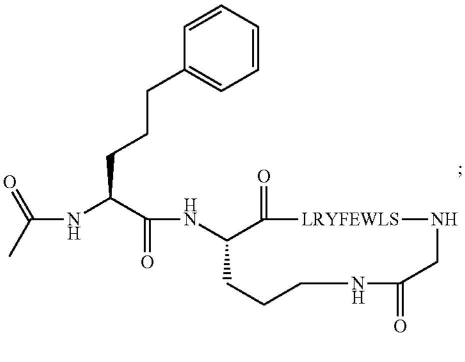

;

(SEQ ID NO: 2)

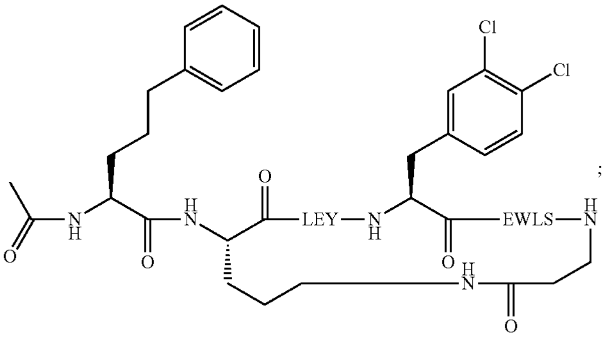

;

-continued
(SEQ ID NO: 3)
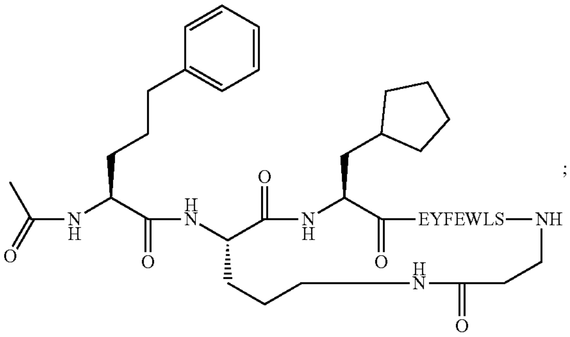
;
(SEQ ID NO: 4)
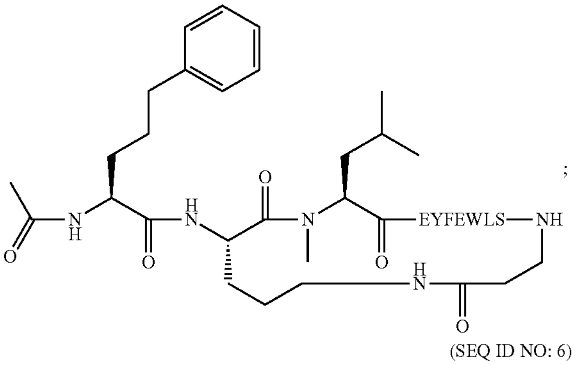
;
(SEQ ID NO: 6)
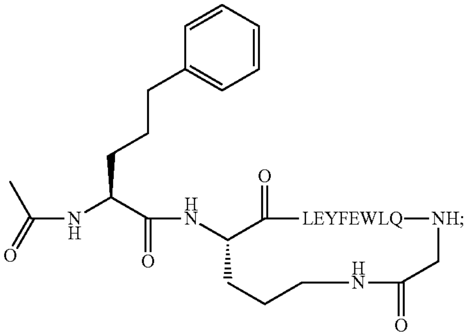
(SEQ ID NO: 9)
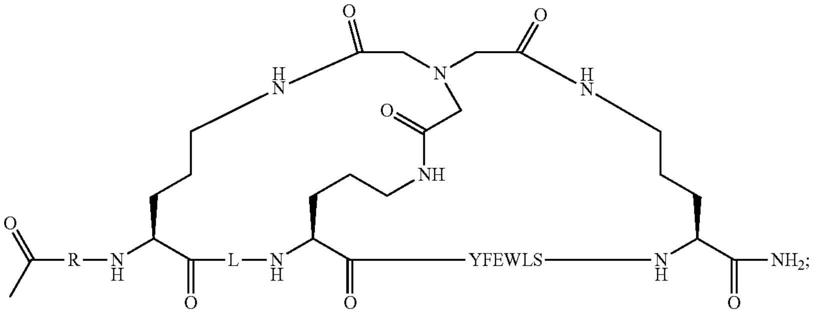
(SEQ ID NO: 7)
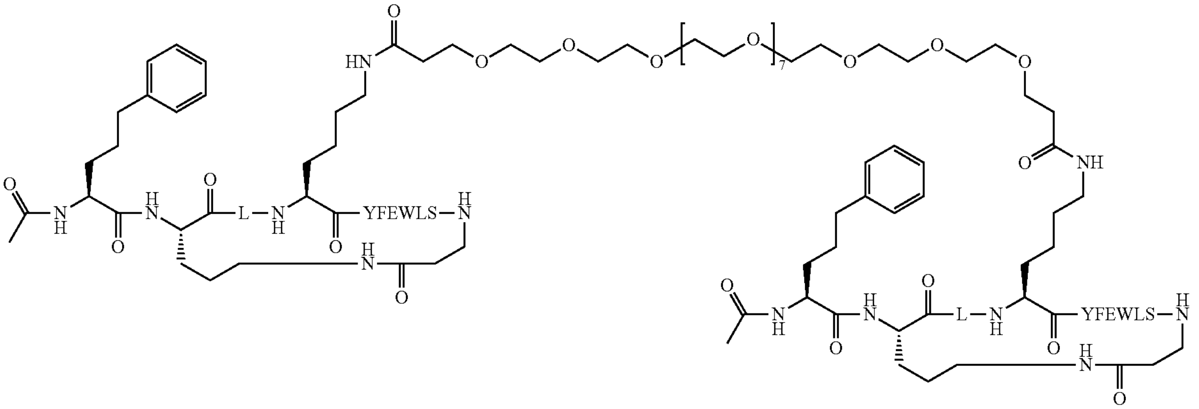
(SEQ ID NO: 5)

The peptidomimetic compounds of the present invention may be prepared by any well know procedure in the art, in particular by the well-established chemical synthesis procedures utilizing automated solid-phase peptide synthesizers followed by chromatographic purification, e.g. as described in the Examples below.

The invention further provides pharmaceutical compositions comprising one or more compounds as described herein and a pharmaceutically acceptable carrier or diluent. A "pharmaceutically acceptable excipient" may be any inert substance that is combined with an active molecule such as a compound according to the invention for preparing a suitable composition. The pharmaceutically acceptable excipient is an excipient that is non-toxic to recipients at the used dosages and concentrations, and is compatible with other ingredients of the formulation. Pharmaceutically acceptable excipients are widely applied and known in the art. The pharmaceutical compositions according to the invention may further comprise at least one other therapeutic, prophylactic and/or diagnostic agent. Said further therapeutic and/or prophylactic agents may for example be agents that are also capable of preventing and/or treating an influenza virus infection, such as for example M2 inhibitors (e.g., amantidine, rimantadine) and/or neuraminidase inhibitors (e.g., zanamivir, oseltamivir). These can be used in combination with the compounds of the invention. "In combination" herein means simultaneously, as separate formulations, or as one single combined formulation, or according to a sequential administration regimen as separate formulations, in any order.

In a further aspect, the present invention provides compounds as described herein for use in the diagnosis, prevention and/or treatment of influenza. The invention furthermore provides the use of a compound as described herein in the manufacture of a medicament for the diagnosis, prevention and/or treatment of influenza. As used herein, the term "influenza", or "influenza virus disease" refers to the pathological condition resulting from an infection of a cell or a subject by an influenza virus. In specific embodiments, the term refers to a respiratory illness caused by an influenza virus. As used herein, the term "influenza virus infection" means the invasion by, multiplication and/or presence of an influenza virus in a cell or a subject. Influenza virus infections can occur in small populations, but can also spread around the world in seasonal epidemics or, worse, in global pandemics where millions of individuals are at risk. The invention provides binding molecules that can neutralize the infection of influenza strains that cause such seasonal epidemics, as well as potential pandemics.

The invention further provides methods for preventing and/or treating influenza in a subject, comprising administering a therapeutically effective amount of a compound as described herein to a subject in need thereof. The term "therapeutically effective amount" refers to an amount of the compound as defined herein that is effective for preventing, ameliorating and/or treating a condition resulting from infection with an influenza virus. Prevention and/or treatment may be targeted at patient groups that are susceptible to influenza infection. Such patient groups include, but are not limited to e.g., the elderly (e.g. ≥50 years old, ≥60 years old, and preferably ≥65 years old), the young (e.g. ≤5 years old, ≤1 year old), hospitalized patients and already infected patients who have been treated with an antiviral compound but have shown an inadequate antiviral response.

The compounds of the invention may be administered to a subject for example intravenously, intranasally, via oral inhalation, pulmonary, subcutaneously, intradermally, intravitreally, orally, intramuscularly etc. The optimal route of administration will be influenced by several factors including the physicochemical properties of the active molecules, the urgency of the clinical situation and the relationship of the plasma concentrations of the active molecules to the desired therapeutic effect.

The present invention further provides a method of detecting an influenza A virus in a sample, wherein the method comprises the steps of a) contacting said sample with a diagnostically effective amount of a compound according to the invention, and b) determining whether the compound specifically binds to a molecule in the sample. The sample may be a biological sample including, but not limited to blood, serum, tissue or other biological material from (potentially) infected subjects. The (potentially) infected subjects may be human subjects, but also animals that are suspected as carriers of influenza virus might be tested for the presence of influenza virus using the compounds of the invention.

The present invention is further illustrated in the following, non-limiting Examples.

EXAMPLES

Example 1: Synthesis of CP132070

(SEQ ID NO: 1)

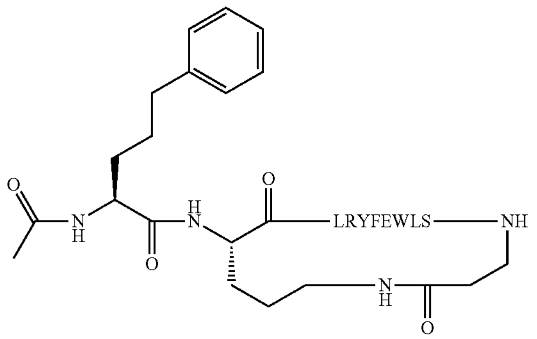

The linear peptide precursor was prepared by manual solid phase Fmoc peptide synthesis on a 0.5 mmol scale by using beta alanine preloaded 2-chlorotrityl chloride resin (0.685 mmol/g). Amino acid side-chain functionalities were protected as N-Boc (W), O-t-Bu (E,S,Y) and N-Pbf (R) groups. The N-Dde group was used for the orthogonal protection of the ornithine side-chain amine functionality (Boc: tert. Butoxycarbonyl, t-Bu: tert. Butyl, Dde: 1-(4,4-dimethyl-2,6-dioxacyclohexylidene)ethyl, Fmoc: 9-Fluorenylmethoxycarbonyl, Pbf: 2,2,4,6,7-Pentamethyldihydrobenzofuran-5-sulfonyl). Prior to attachment of the first amino acid, the resin was swelled in DMF (dimethylformamide) for 1 h. A coupling protocol using 3 equivalents of each Fmoc-amino acid in DMF (4 mL), and an activation mixture containing HBTU ((2-(1H-benzotriazole-1-yl)-1,1,3,3-tetramethyluronium hexafluorophosphate, 2.85 eq.) and DIPEA (N,N-diisopropylethylamine, 6 eq.) in DMF (4 mL) was employed. The reaction mixture was shaken for 1.5-2 hours. Fmoc-group removal was performed with a 20% piperidine solution in DMF (2×15 min). N-terminal acetylation was performed at the end of the peptide assembly by treatment of the peptide-resin with a mixture of acetic anhydride and 4-methylmorpholine in DMF (2:1:17, v/v/v, 20 mL) at room temperature for 1 hour. Finally, the N-Dde protecting group was selectively removed by treating the peptide-resin with a 3% hydrazine hydrate solution in DMF (3×10 min).

The ornithine side-chain deprotected peptide was cleaved from the resin by swirling the peptide-resin for 60 minutes in a mixture of 65% (v) DCM (dichloromethane), 20% (v) hexafluoroisopropanol, 10% (v) trifluoroethanol and 5% (v) triethylsilane (10 mL/g peptide-resin). The resin was filtered off and washed with DCM. The peptide was precipitated from the filtrate by the addition of cold isopropyl ether, and dried under vacuum. The crude peptide was used as such in the subsequent lactam cyclization step.

Lactam cyclization was performed at high dilution by dissolving the ornithine side-chain deprotected C-terminal carboxylic acid peptide in 150 mL of DMF, to which a solution of PyBOP (benzotriazol-1-yl-oxytripyrrolidino-phosphonium hexafluorophosphate, 2 eq.) and N-methyl-morpholine (6 eq.) in DMF (90 mL) was added dropwise. The reaction mixture was stirred at room temperature until complete conversion was observed. Removal of the solvent under reduced pressure afforded the cyclized peptide which was completely deprotected by treatment with a mixture of 90% (v) TFA (trifluoroacetic acid), 5% (v) thioanisole, 2.5% (v) $H_2O$ and 2.5% (v) EDT (ethanedithiol) at room temperature for three hours. Precipitation, followed by washing with ice-cold diethyl ether afforded the crude peptide which was purified by reversed-phase high performance liquid chromatography (RP-HPLC) on a Luna C18 preparative HPLC column (25×200 mm, 10 μm, 100 Å) in tandem with a Gemini C18 preparative HPLC column (30×150 mm, 50 μm, 100 Å) with a mobile phase flow rate of 20 mL/min (mobile phase A: 0.05% TFA in water, mobile phase B: $CH_3CN$, a linear gradient was applied). Lyophilization of the pure fractions yielded 328 mg (yield: 53%, purity: 97%) of the lactam cyclized peptide as the trifluoroacetate salt.

The compounds below were prepared in analogy to CP132070:

(SEQ ID NO: 2)

CP141019

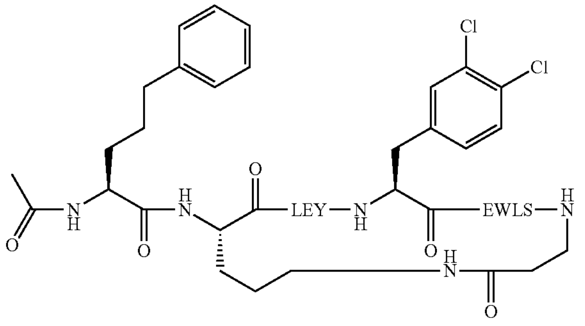

-continued (SEQ ID NO: 3)

CP141036

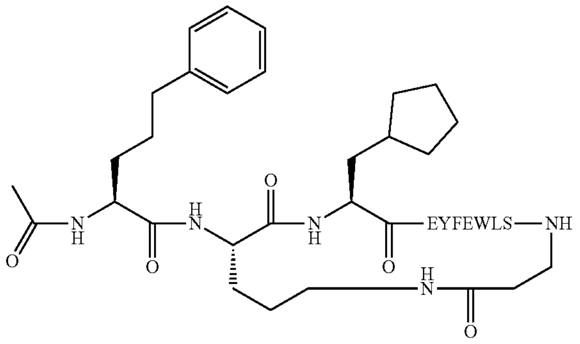

(SEQ ID NO: 4)

CP141037

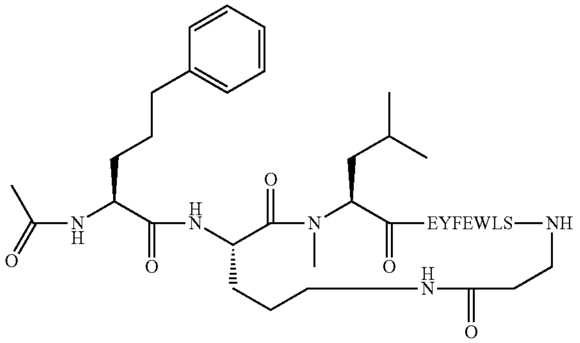

(SEQ ID NO: 6)

CP141077

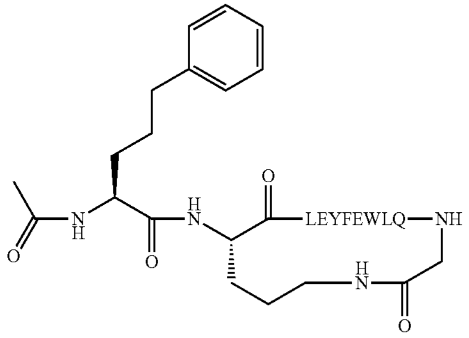

Example 2: Synthesis of CP141032

(SEQ ID NO: 9)

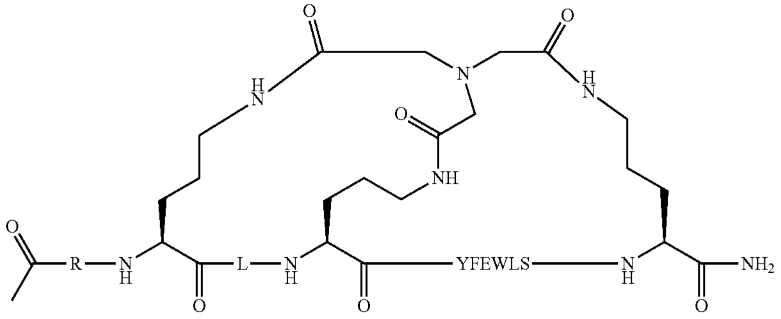

The linear peptide precursor was prepared by manual solid phase Fmoc peptide synthesis on a 0.25 mmol scale by using Sieber resin (0.69 mmol/g). Amino acid side-chain functionalities were protected as N-Boc (W), O-t-Bu (E,S, Y) and N-Pbf (R) groups. The N-Dde group was used for the orthogonal protection of the ornithine side-chain amine functionalities (Boc: tert. Butoxycarbonyl, t-Bu: tert. Butyl, Dde: 1-(4,4-dimethyl-2,6-dioxacyclohexylidene)ethyl, Fmoc: 9-Fluorenylmethoxycarbonyl, Pbf: 2,2,4,6,7-Pentamethyldihydro-benzofuran-5-sulfonyl). Prior to attachment of the first amino acid, the resin was swelled in DMF for 1 h. A coupling protocol using 3 equivalents of Fmoc-amino acid in DMF (4 mL), and an activation mixture containing 2.85 equivalents of HBTU and 6 equivalents of DIPEA in DMF (4 mL) was employed; the reaction mixture was shaken for 1.5-2 hours during each coupling step. Fmoc-group removal was performed with a 20% piperidine solution in DMF (2×15 min). N-terminal acetylation was performed at the end of the peptide assembly by treatment of the peptide-resin with a mixture of acetic anhydride and 4-methylmorpholine in DMF (2:1:17, v/v/v, 20 mL) at room temperature for 1 hour. Finally, the N-Dde protecting groups were selectively removed by treating the peptide-resin with a 3% hydrazine hydrate solution in DMF (3×10 min), after which the peptide-resin was washed with DMF and DCM.

Subsequent cleavage of the peptide from the resin was done by swirling the peptide-resin for 60 minutes in a solution of DCM containing 1% of TFA. The resin was filtered off and washed with DCM. The filtrate was poured into cold isopropyl ether resulting in the precipitation of the peptide. Isolation by centrifugation, washing with cold isopropyl ether and drying under vacuum, yielded 348 mg (yield: 55%, purity: 80%) of the crude linear peptide, which was used as such in the TSAT (tris-(succinimidyl)aminotriacetate) mediated cyclization step.

The ornithine side chain deprotected peptide (150 mg 80% purity, 0.0595 mmol) was dissolved in DMF (300 mL), followed by the addition of DIPEA until pH=8-9. To this mixture, a solution of the TSAT cross linking reagent (1.0 eq) in DMF (50 mL) was added dropwise, the resulting reaction mixture was stirred at room temperature until complete conversion was observed. Removal of the solvent under reduced pressure afforded the bicyclic peptide which was completely deprotected by treatment with a mixture of 90% (v) TFA, 5% (v) thioanisole, 2.5% (v) $H_2O$ and 2.5% (v) EDT at room temperature for three hours. Precipitation and washing with ice-cold tert-butyl methyl ether afforded the crude cyclic peptide which was purified by reversed-phase high performance liquid chromatography (RP-HPLC) as described in example 1. Lyophilization of the pure fractions gave 40 mg (yield: 34%, purity 94%) of bicyclic peptide CP141032 as the trifluoroacetate salt.

Example 3: Synthesis of the Homodimeric Peptide CP141100

(SEQ ID NO: 7)

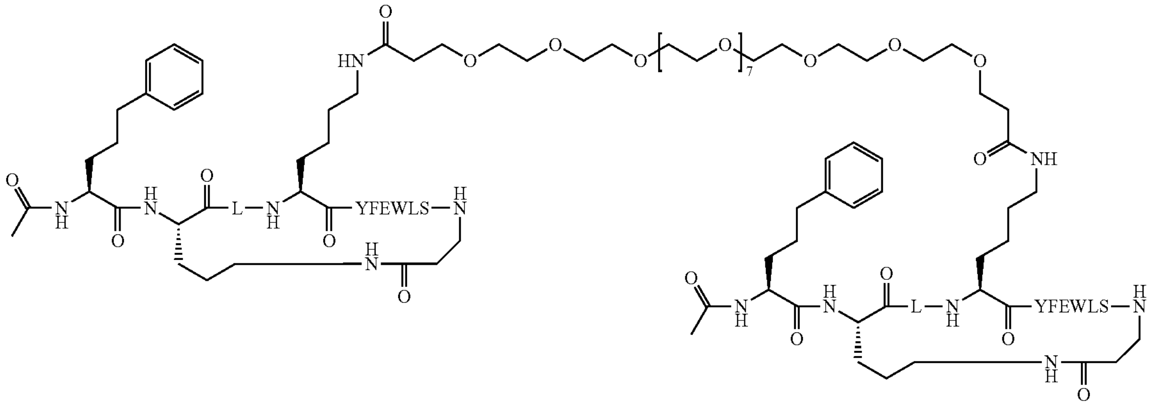

The linear monomeric peptide precursor was prepared by automated solid phase Fmoc peptide synthesis on a beta alanine preloaded 2-chlorotrityl chloride resin (0.29 mmol/ g) on a 0.5 mmol scale. Amino acid side-chain functionalities were protected as N-Boc (W) and O-t-Bu (E,S,Y) groups. The N-Mtt group was used for the orthogonal protection of the ornithine side-chain amine functionality (Boc: tert. Butoxycarbonyl, t-Bu: tert. Butyl, Fmoc: 9-Fluorenylmethoxycarbonyl, Mtt: Methyltrityl). Prior to attachment of the first amino acid, the resin was swelled in NMP (2×15 min). A coupling protocol using 10 equivalents of Fmoc-amino acid, 9 equivalents of HATU (N,N,N',N'-tetramethyl-O-(7-azabenzotriazol-1-yl)uronium hexafluorophosphate, 0.45 M in DMF) and 10 equivalents of DIPEA (2M in NMP) was employed for very amino acid coupling step (duration of coupling: 30 minutes). A double coupling strategy was applied in case of the two N-terminal amino acids. Fmoc removal was done with a 20% piperidine solution in NMP and monitored by UV detection. N-terminal acetylation was performed at the end of the peptide assembly by treatment with an excess of acetic anhydride in the presence of DIPEA (10 eq. of a 2M solution in NMP) for 30 minutes.

Peptide cleavage from the resin and selective Mtt side chain deprotection was accomplished by swirling the peptide-resin for 60 minutes in a mixture of 65% (v) DCM (dichloromethane), 20% (v) hexafluoroisopropanol, 10% (v) trifluoroethanol and 5% (v) triethylsilane (10 mL/g peptide-resin). The resin was filtered off and washed with DCM. The peptide was precipitated from the filtrate by the addition of cold diethyl ether, the crude product was dried under vacuum and used as such in the next step.

Lactam cyclization was performed at high dilution by dissolving the crude, ornithine side-chain deprotected peptide in 200 mL of DMF, followed by the dropwise addition of a solution of PyBOP (2 eq.) and N-methylmorpholine (6 eq.) in DMF (60 mL). The reaction mixture was stirred at room temperature until complete conversion was observed (2 hours). The solvent was removed under reduced pressure and the residue was re-dissolved in ethyl acetate. The organic phase was washed with an aqueous 5% $NaHCO_3$ solution and brine, and concentrated under reduced pressure. The cyclized peptide was completely deprotected by treatment with a mixture of 87.5% (v) TFA, 5% (v) thioanisole, 5% (v) $H_2O$ and 2.5% (v) EDT at room temperature for two hours. Precipitation, followed by washing with ice-cold diethyl ether afforded the crude peptide which was purified by reversed-phase high performance liquid chromatography (RP-HPLC) on a XBridge C18 OBD preparative HPLC column (30×250 mm, 5 μm, 140 Å) with a mobile phase flow rate of 30 mL/min (solvent A: 0.1% TFA in water+ $CH_3CN$, solvent B: $CH_3CN$, a linear gradient was applied). Lyophilization of the pure fractions afforded 250 mg (yield 31%, purity: 83%) of the fully side-chain deprotected lactam cyclized peptide as the trifluoroacetate salt.

Dimerization was performed using the commercially available bis-PEG13-NHS ester (bis-succinimidyl activated bis-PEG13-acid) as linkage reagent. This was done by adding the linkage reagent (0.4 eq.) to a solution of the lactam cyclized peptide (75 mg, 0.048 mmol) and $Et_3N$ (5 eq.) in dry DMF, the reaction mixture was stirred at room temperature until no more conversion was observed. The solvent was removed under reduced pressure and the resulting residue was directly purified by reversed-phase high performance liquid chromatography (RP-HPLC) as described above. Lyophilization of the pure fractions gave 19 mg (yield: 11%, purity 96%) of dimeric peptide CP141100.

Example 4: Synthesis of CP141066

(SEQ ID NO: 5)

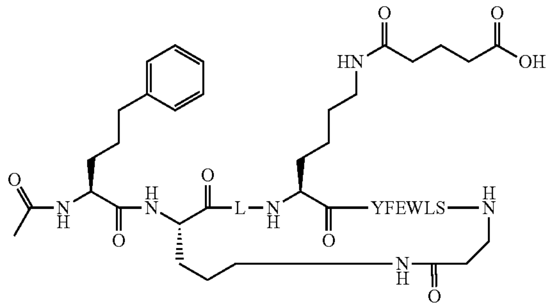

The fully side-chain deprotected lactam cyclized peptide intermediate (50 mg, 0.032 mmol) from example 3 was dissolved in DMF (2 mL). $Et_3N$ (5 eq.) and disuccinimidyl glutarate (1.0 eq.) were added, and the reaction mixture was stirred at room temperature overnight. The solvent was removed under reduced pressure and the resulting residue was purified by reversed-phase high performance liquid chromatography as described in example 3. Lyophilization of the pure fractions gave 28 mg (yield: 56%, purity 99%) of peptide CP141066.

Example 5: Synthesis of the Lactam Cyclized Peptide CP141099

(SEQ ID NO: 8)

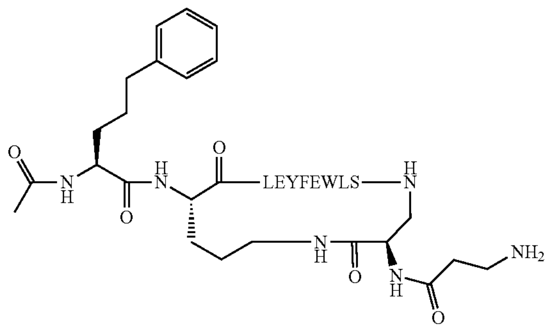

The linear peptide was synthesized on a 0.3 mmol scale, by automated Fmoc solid phase peptide synthesis on a L-Dap(Fmoc) (Dap: 2,3-diaminopropionic acid) preloaded 2-chlorotrityl chloride resin (0.15 mmol/g). The L-Dap (Fmoc) preloaded 2-chlorotrityl chloride resin was manually prepared by treating 2-chlorotrityl chloride resin (5 g, 1.4 mmol/g, 7 mmol) with a DMF solution of Dde-L-Dap (Fmoc)-OH (0.66 eq.) in the presence of DIPEA (2.6 eq.). The resulting reaction mixture was shaken for 90 minutes, methanol (2.5 ml) was added, and shaking was continued for an extra 5 minutes. The solvent was removed by filtration and the resin was washed with DMF (5×). Finally, the N-Dde protecting group was removed by reaction with a 2% hydrazine hydrate solution in DMF (5×2 min), affording the L-Dap(Fmoc) loaded 2-chlorotrityl chloride resin with a substitution rate of 0.15 mmol/g (The substitution rate was determined photometrically from the amount of Fmoc chromophore released upon treatment of the resin with a piperidine solution in DMF.). Subsequent amino acid couplings and N-terminal acetylation were done by automated synthesis as described in example 3. It is important to note that Boc-beta-alanine was coupled prior to Fmoc deprotection of the L-Dap(Fmoc) preloaded 2-chlorotrityl chloride resin.

Peptide cleavage from the resin and selective Mtt side chain deprotection was accomplished by swirling the peptide-resin for 60 minutes in a mixture of 65% (v) DCM, 20% (v) hexafluoroisopropanol, 10% (v) trifluoroethanol and 5% (v) triethylsilane (10 mL/g peptide-resin). The resin was filtered off and washed with DCM. The peptide was precipitated from the filtrate by the addition of cold diethyl ether, the crude product was dried under vacuum and used as such in the next step.

Lactam cyclization was performed at high dilution by dissolving the crude, ornithine side-chain deprotected peptide in 120 mL of DMF, followed by the dropwise addition of a solution of PyBOP (2 eq.) and N-methylmorpholine (6 eq.) in DMF (36 mL). The reaction mixture was stirred at room temperature until complete conversion (2 hours). The solvent was removed under reduced pressure and the residue was re-dissolved in ethyl acetate. The organic phase was washed with an aqueous 5% $NaHCO_3$ solution and brine, and concentrated under reduced pressure. Full side chain deprotection was performed by treatment with a mixture of 87.5% (v) TFA, 5% (v) thioanisole, 5% (v) $H_2O$ and 2.5% (v) EDT at room temperature for two hours. Precipitation, followed by washing with ice-cold diethyl ether afforded the crude peptide which was purified by reversed-phase high performance liquid chromatography on a XBridge C18 OBD preparative HPLC column (30×250 mm, 5 μm, 140 Å) with a mobile phase flow rate of 20 mL/min (solvent A: 0.1% TFA in water+$CH_3CN$, solvent B: MeOH, a linear gradient was applied). Lyophilization of the pure fractions afforded 36 mg (yield 7%, purity: 95%) of the lactam cyclized peptide CP141099 as the trifluoroacetate salt.

Example 6: Peptide Analysis

UPLC (Ultra Performance Liquid Chromatography) and HPLC (High Performance Liquid Chromatography) (HPLC) measurements were performed using a LC pump, a diode-array (DAD) or a UV detector and a column as specified in the respective methods. If necessary, additional detectors were included (see table of methods below). Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's molecular weight (MW). Data acquisition was performed with appropriate software.

Peptides are described by their experimental retention time (Rt) and their molecular weight (MW). All results were obtained with experimental uncertainties that are commonly associated with the method used. As used herein: "MSD": Mass Selective Detector, "DAD": Diode Array Detector, "SQD": Single Quad Detector.

TABLE 1

LCMS Method codes (Flow expressed in mL/min; column temperature (T) in ° C.; Run time in minutes).

| Method code | Instrument | Column | Mobile phase | Gradient | Flow / Col T | Run time |
|---|---|---|---|---|---|---|
| A | Agilent: 1200 HPLC—DAD and MSD | Agilent: ZORBAX Eclipse XDB-C18 (5 μm, 4.6*150 mm) | A: 0.1% TFA in $H_2O$ B: 0.05% TFA in $CH_3CN$ | 70% A to 40% A in 20 min, to 20% A in 5 min. | 0.8 / 30 | 25 |
| B | Agilent: 1200 HPLC—DAD and MSD | Agilent: ZORBAX Eclipse XDB-C18 (5 μm, 4.6*150 mm) | A: 0.1% TFA in $H_2O$ B: 0.05% TFA in $CH_3CN$ | 90% A to 50% A in 20 min, to 10% A in 15 min. | 0.8 / 30 | 25 |
| C | Waters: Acquity ® UPLC ®—DAD and SQD | BEH300C4 Column (1.7 μm, 2.1 × 150 mm; Waters Acquity ® | A: 0.1% HCOOH + 5% $CH_3OH$ in $H_2O$ B: $CH_3OH$ | From 95% A to 5% A in 14.0 min and hold 1 min | 0.2 / 30 | 15 |

TABLE 2

Peptide Analysis

| Comp. ID | $R_t$ (min) # | Calculated MW | Purity (%)$ |
|---|---|---|---|
| CP141099 | 7.80 (C) | 1556.77 | 95 |
| CP141019 | 15.34 (A) | 1539.57 | 100 |
| CP141037 | 14.10 (A) | 1484.71 | 99 |
| CP141066 | 7.12 (C) | 1583.84 | 99 |
| CP132070 | 14.07 (A) | 1497.75 | 97 |
| CP141036 | 14.01 (A) | 1496.72 | 98 |
| CP141077 | 12.63 (C) | 1511.73 | 99 |
| CP141100 | 8.64 (C) | 3594.22 | 96 |
| CP141032 | 16.04 (B) | 1633.86 | 94 |

Analytical methods (A, B, C) indicated in parentheses are described above.

$Peptide purity is calculated as the area percentage of UV-positive (220 nm) material eluted under the main peak of the chromatogram.

Example 7: Binding of Compounds to Influenza HA and Competition of Compounds with Other HA Binders Binding competition studies were designed to test compounds for competition with other well characterized HA binding proteins (including e.g. CR9114) with known epitopes on HA. The epitopes where either located at the stem of the HA (viral membrane proximal part of HA) or, for control purposes, at the head of HA (viral membrane distal part of HA). If competition was observed, it is assumed that both molecules bind to a similar or at least overlapping epitope at the surface of HA. Competition with a HA head- and stem-binder was interpreted as unspecific binding.

Hereto an AlphaLISA competition assay (Perkin Elmer) was established which relied on biotinylated full length and trimeric HA proteins (Protein Sciences, 10 μL, 0.5 nM final concentration in 50 μL) bound by HA-specific binders. The interaction between HA and the binder was detected after 1 h incubation at room temperature (RT) with two beads, a streptavidin donor bead recognizing HA (10 μL of 10 μg/mL) and an anti Fc bead (10 μg/mL) recognizing the IgGs used. If after an additional hour of incubation at RT the excited donor bead (680 nm) and acceptor bead are in close proximity, an energy transfer (singlet oxygen) can be measured as a luminescence signal of the acceptor bead (Perkin Elmer EnVision plate reader). The signal intensity in this homogeneous assay format is directly proportional to the binding strength (affinity/avidity) between both binding partners. A competitor (compound), depending on its affinity and concentration (usually tested in a range from 100 nM to 0.5 pM) can disrupt the AlphaLISA signal leading to a sigmoidal inhibitor curve which is fitted with a standard four parameter logistic nonlinear regression model in SPSS. Averages of calculated pIC50 values are shown in Table 3.

TABLE 3

Compound competition for binding to influenza A virus HA (values represent averages of $pIC_{50}$, the negative log of the half maximal inhibitory concentration, higher values indicate exponentially greater potency, empty cells mean 'not tested')

| | H1 | | | | | H5 | |
|---|---|---|---|---|---|---|---|
| Compound | A/New Caledonia/20/1999 HA + Stem-binder | A/California/07/2009 HA + Head-binder | A/California/07/2009 HA + Stem-binder | A/Brisbane/59/07 HA + Stem-binder | A/South Carolina/20/18 HA + Stem-binder | A/Vietnam/1203/04 HA + Stem-binder | H2 A/Singapore/1/57 HA + Stem-binder |
| CP132070 | 6.75 | <4.30 | 6.54 | | | 7.16 | |
| CP141019 | 7.30 | <4.30 | 7.15 | 7.33 | 7.10 | 7.39 | 6.05 |
| CP141036 | 6.87 | <4.30 | 6.40 | 6.84 | 6.26 | 7.19 | 5.56 |
| CP141037 | 7.09 | <4.30 | 6.69 | 7.06 | 6.82 | 7.21 | 5.54 |
| CP141066 | 6.73 | <4.30 | 6.61 | | | 6.93 | |
| CP141077 | 6.75 | <4.30 | 6.37 | 6.59 | 6.29 | 6.65 | 5.53 |
| CP141099 | 7.56 | <4.30 | 7.23 | 7.17 | 7.09 | 7.35 | 5.94 |
| CP141100 | 6.19 | <4.30 | 6.24 | 5.88 | 5.13 | 6.76 | 4.53 |
| CP141032 | 5.65 | <4.30 | 5.02 | | | 5.59 | |

In conclusion, according to the invention it has been shown that the compounds of the invention bind broadly to group 1 influenza A viruses and specifically compete with HA stem-binding molecules but not with control HA head-binding molecules.

Example 8: Influenza Virus Neutralizing Activity and Cell Toxicity of Compounds Compounds were analyzed in a virus neutralization assay (VNA) for their ability to prevent influenza virus infection of mammalian cells. For this purpose, human lung epithelia derived Calu-3 cells (ATCC, cat # HTB-55) were seeded in 96-well plates (4E+04 cells/well) and incubated for at least 7 days at 37° C. and 10% $CO_2$ in complete DMEM (containing 1×MEM Non-Essential Amino Acids, 2 mM L-Glutamine, and 10% FBSHI origin: Australia; Gibco). Polarized Calu-3 cells at about 90% confluency and established tight junctions are ready for the VNA. On the day of the assay, sample dilutions plates are prepared from compound stock (dissolved in PBS 0.1% BSA, 0.1% Tween 5% DMSO, 500 nM start concentration) 2 fold diluted in incomplete DMEM (containing 2 mM L-glutamine, 1× pen/strep). Sample dilution plates are centrifuged (1000 g for 15 min) to remove potential aggregates. 5 $TCID_{50}$/50 μL influenza virus (pre-titrated on Calu-3 cells) in incomplete DMEM is then added to the sample dilution plate and incubated for 1 hour at 37° C. and 10% $CO_2$. Remove medium from cells and replace with 50 μL incomplete DMEM supplemented with 3% FBS. 100 μL Virus/compound mix is then added to the cells resulting in a total assay volume of 150 μL with a final concentration of 1% FBS. After incubating for 4 days at 37° C. and 10% $CO_2$ cells are washed with PBS and fixed with 200 μL/well 80% Acetone for 15 min at room temperature (RT). The level of influenza infection is determined influenza nucleoprotein (NP) ELISA. The primary antibody anti-Flu-A-NP (Abbiotec, Clone 5D8) was used at 1:1000 diluted in 1% BSA in PBS and incubated for 1 hour shaking at 300 rpm at RT. After washing the cells three times with wash-buffer (PBS, 0.05% Tween), the secondary antibody (anti-Mouse HRP, 1:2000) is added and incubated for 1 hour shaking at 300 rpm at RT. After washing the cells three times, 50 μL/well POD chemiluminescence substrate is added and incubate for 2-5 min before reading luminescence on the Biotek Synergy Neo Plate Reader. The $pIC_{50}$ of compounds was calculated with the SPSS software. Multiple influenza strains in repeats were tested to assess the breadth of neutralization (see Table 4).

To determine the level of cell toxicity the VNA was also performed in the absence of virus. Cytopathic effect (CPE) was measured via ATP Lite reagent and according to manufacturer's protocol (Perkin Elmer) and the data analyzed in the same way (see Table 4).

TABLE 4

Influenza virus neutralizing compounds (values represent averages of $pIC_{50}$, the negative log of the half maximal inhibitory concentration, higher values indicate exponentially greater potency, empty cells mean 'not tested')

| Compound | Toxicity | VNA H1N1 A/California/07/09 | VNA H1N1 A/New Caledonia/20/99 | VNA H5N1 A/Vietnam/1194/04 |
|---|---|---|---|---|
| CP132070 | <4.00 | <4.00 | 4.08 | 4.42 |
| CP141019 | <4.00 | 7.66 | 7.16 | 7.09 |
| CP141036 | <4.00 | 4.02 | 5.86 | 6.77 |
| CP141037 | <4.00 | 4.13 | 6.29 | 6.17 |

TABLE 4-continued

Influenza virus neutralizing compounds (values represent averages of $pIC_{50}$, the negative log of the half maximal inhibitory concentration, higher values indicate exponentially greater potency, empty cells mean 'not tested')

| Compound | Toxicity | VNA H1N1 A/California/07/09 | VNA H1N1 A/New Caledonia/20/99 | VNA H5N1 A/Vietnam/1194/04 |
|---|---|---|---|---|
| CP141066 | <4.00 | <4.00 | 4.38 | 4.32 |
| CP141070 | <4.00 | 4.17 | 4.18 | <4.00 |
| CP141077 | <4.00 | 4.25 | 4.98 | 5.35 |
| CP141100 | <4.00 | 7.49 | 7.60 | 7.80 |
| CP141032 | <4.00 | | 4.23 | <4.00 |

In conclusion, the compounds of the invention broadly neutralize influenza virus group 1 strains in the absence of detectable cell toxicity.

TABLE 5

Standard amino acids, abbreviations and properties

| Amino Acid | 3-Letter | 1-Letter | Side chain polarity | Side chain charge (pH 7.4) |
|---|---|---|---|---|
| alanine | Ala | A | non-polar | Neutral |
| arginine | Arg | R | polar | Positive |
| asparagine | Asn | N | polar | Neutral |
| aspartic acid | Asp | D | polar | Negative |
| cysteine | Cys | C | non-polar | Neutral |
| glutamic acid | Glu | E | polar | Negative |
| glutamine | Gln | Q | polar | Neutral |
| glycine | Gly | G | non-polar | Neutral |
| histidine | His | H | polar | positive(10%) neutral(90%) |
| isoleucine | Ile | I | non-polar | Neutral |
| leucine | Leu | L | non-polar | Neutral |
| lysine | Lys | K | polar | Positive |
| methionine | Met | M | non-polar | Neutral |
| phenylalanine | Phe | F | non-polar | Neutral |
| proline | Pro | P | non-polar | Neutral |
| serine | Ser | S | polar | Neutral |
| threonine | Thr | T | polar | Neutral |
| tryptophan | Trp | W | non-polar | Neutral |
| tyrosine | Tyr | Y | polar | Neutral |
| valine | Val | V | non-polar | Neutral |

Example 9: Direct HA Binding Experiments with Surface Plasmon Resonance (SPR)

All SPR experiments were performed using a Biacore T200 instrument (GE Healthcare) operated at 25° C. Trimeric HA proteins (Protein Sciences) were randomly-biotinylated and covalently immobilized to a streptavidin coated carboxymethylated dextran sensor surface (SA chip, GE Healthcare). Test compounds were resuspended in running buffer (20 mM PBS, 137 mM NaCl, 0.05% P-20 surfactant, pH 7.4 (GE Healthcare), supplemented 2% DMSO) and binding constants were obtained from a series of injections of compounds at a concentration range of 0.1 nM to 10 µM with a flow rate of 30 µl/min. Data from single-cycle kinetics was analyzed using BIAevaluation software. Base lines were adjusted to zero for all curves, and injection start times were aligned. The reference sensorgrams were subtracted from the experimental sensorgrams to yield curves representing specific binding followed by background subtraction (i.e. double-referencing). Binding kinetics were evaluated using a 1:1 binding model (Langmuir) to obtain association (ka) and dissociation rate (kd) constants. Binding affinity (KD) was estimated from the concentration dependence of the observed steady-state responses. Experiments were performed three times to ensure reproducibility.

Binding curves for representative experiments for three compounds binding to HA's from three influenza strains (A/California/07/09 (H1), A/New Caledonia/20/99 (H1), and A/Vietnam/1194/04 (H5)) are presented in FIG. 1. Binding affinities between 10 and 100 nM were detected for all three compounds, with dissociation rates between 5 $s^{-1}$ and 20 $s^{-1}$, depending on the HA strain, as presented in Table 6.

TABLE 6 pKD values with a standard deviation SD_pKD and corresponding dissociation rate kd [s−1] for CP141037, CP141019 and CP141099. Each compound has been tested for binding to HA derived from three influenza strains (A/California/07/09 (H1) and A/New Caledonia/20/99 (H1) and A/Vietnam/1194/04 (H5).

| Compound | HA | $pK_D$ | $SD\_pK_D$ | $k_d$ ($s^{-1}$) |
|---|---|---|---|---|
| CP141037 | A/California/07/09 (H1) | 7.21 | 0.14 | 1.84E-01 |
| CP141037 | A/New Caledonia/20/99 (H1) | 7.35 | 0.16 | 7.53E-02 |
| CP141037 | A/Vietnam/1194/04 (H5) | 7.19 | 0.33 | 8.45E-02 |
| CP141019 | A/California/07/09 (H1) | 7.77 | 0.11 | 1.82E-01 |
| CP141019 | A/New Caledonia/20/99 (H1) | 7.75 | 0.13 | 5.89E-02 |
| CP141019 | A/Vietnam/1194/04 (H5) | 7.50 | 0.29 | 5.33E-02 |
| CP141099 | A/California/07/09 (H1) | 7.58 | 0.16 | 2.52E-01 |
| CP141099 | A/New Caledonia/20/99 (H1) | 7.60 | 0.18 | 1.01E-01 |
| CP141099 | A/Vietnam/1194/04 (H5) | 7.56 | 0.35 | 6.52E-02 |

The invention claimed is:

1. A peptidomimetic compound having the sequence:

Cap1-X1-X2-X3-X4-X5-X6-X7-X8-Leu-X9-X10-Cap2 wherein:

Cap1 is an amino acid sequence comprising from 0-10 residues with a N-terminal blocking group;

X1 is any L or D-amino acid;

X2 is any L-amino acid;

X3 is an aliphatic L-amino acid with a molecular weight below 200 Da;

X4 is any L-amino acid;

X5 is Tyr or a L-tyrosine analog;

X6 is Phe or a L-phenylalanine analog;

X7 is any charged or neutral hydrophilic L-amino acid;

X8 is Trp or a L-tryptophan analog;

X9 is absent or any hydrophilic L-amino acid;

X10 is any L-amino acid; and

Cap2 is an amino acid sequence comprising from 0-10 residues with a C-terminal blocking group, and wherein the compound is capable of specifically binding to hemagglutinin (HA) of at least two influenza A virus strains comprising HA of two different subtypes from phylogenetic group 1.

2. The peptidomimetic compound according to claim 1, wherein

X3 is an aliphatic L-amino acid with a molecular weight below 200 Da with a linear or C-gamma-branched side chain;

X5 is Tyr or a L-tyrosine analog having a hydrogen bond donor and/or acceptor replacing the hydroxyl group of tyrosine;

X6 is Phe or a L-phenylalanine analog with one or more substituents selected from the group consisting of hydrogen, halogen, a C1-C4 alkyl on the ortho and/or meta position of the phenyl ring, a halogen at the para position of the phenyl ring, L-3-naphthalene-1-yl-alanine; and L-3-naphthalene-2-yl-alanine; and X8 is Trp or a L-tryptophan analog with a halogen substituent at C5, C6 and/or C7, and/or a small aliphatic substituent on C2 of the indole ring.

3. The peptidomimetic compound according to claim 1, wherein the compound is cyclized.

4. The peptidomimetic compound according to claim 1, wherein

X2 and/or X4 is any L-amino acid with a functional group that can be used for cyclization, wherein the functional group is 2-5 atoms away from the C-alpha atom of the L-amino acid; and X10 is any L-amino acid with a functional group that can be used for cyclization, wherein the functional group is 2-5 atoms away from the C-alpha atom of the L-amino acid.

5. The peptidomimetic compound according to claim 3, wherein the compound is cyclized via a chemical bridge between residues X2 and X10.

6. The peptidomimetic compound according to claim 3, wherein the compound is cyclized via the formation of an amide bond comprising residues X2 and X10.

7. The peptidomimetic compound according to claim 6, wherein X2 is Lys or L-ornithine, and X10 is beta-alanine, 3-aminoproprionic acid, 3-amino-2,2-dimethyl-proprionic acid, 4-aminobutanoic acid, 5-aminopentanoic acid, 6-aminohexanoic acid, or Pro.

8. The peptidomimetic compound according to claim 6, wherein X2 is Asp or Glu, and X10 is Lys or L-ornithine.

9. The peptidomimetic compound according to claim 3, wherein the compound is cyclized via a chemical bridge between residues X4 and X10.

10. The peptidomimetic compound according to claim 3, wherein the compound is cyclized via the formation of an amide bond comprising residues X4 and X10.

11. The peptidomimetic compound according to claim 10, wherein X4 is Lys or L-ornithine, and X10 is beta-alanine, 3-aminoproprionic acid, 3-amino-2,2-dimethyl-proprionic acid, 4-aminobutanoic acid, 5-aminopentanoic acid, 6-aminohexanoic acid, or Pro.

12. The peptidomimetic compound according to claim 10, wherein X4 is Asp or Glu, and X10 is Lys or L-ornithine.

13. The peptidomimetic compound according to claim 3, wherein the compound is cyclized via a chemical bridge between residues X2 and X10 and X4 and X10.

14. The peptidomimetic compound according to claim 13, wherein the compound is cyclized by intramolecular cross-linking of free amine groups introduced at residues X2 and X4 and X10 with tris-succinimidyl aminotriacetate (TSAT).

15. A multimeric peptidomimetic compound comprising two or more compounds according to claim 1.

16. The multimeric compound according to claim 15, wherein the compound is dimeric.

17. The multimeric compound according to claim 15, wherein the compound has been dimerized by intermolecular cross-linking of reactive groups introduced at residue X4.

18. The peptidomimetic compound according to claim 1, wherein Cap1 is acetyl or succinyl.

19. The peptidomimetic compound according to claim 1, wherein X1 is (S)-2-amino-5-phenylpentanoic acid, (2S)-3,3-dimethyl-2-amino-5-phenylpentanoic acid or Arg.

20. The peptidomimetic compound according to claim 1, wherein X2 is Lys, L-ornithine, Cys, L-homo-cysteine, or Ser.

21. The peptidomimetic compound according to claim 1, wherein X3 is Leu, L-norleucine, L-cyclopentylalanine, L-cyclobutylalanine, L-cyclopropylalanine, (2S,4S)-2-amino-4-methylhexanoic acid, (2S,4R)-2-amino-4-methylhexanoic acid, (2S,4S)-2-amino-4-methylheptanoic acid, (2S,4R)-2-amino-4-methylheptanoic acid, (S)-2-amino-4-ethylhexanoic acid, and all N-methylated derivatives thereof.

22. The peptidomimetic compound according to claim 1, wherein X4 is Asp, Glu, Arg, Lys, ornithine, cysteine, homocysteine, N6-(4-carboxybutanoyl)lysine, or N5-(4-carboxybutanoyl)ornithine.

23. The peptidomimetic compound according to claim 1, wherein X5 is Tyr.

24. The peptidomimetic compound according to claim 1, wherein X6 is Phe, L-2-chlorophenylalanine, L-3-chlorophenylalanine, L-4-chlorophenylalanine, or L-3,4-dichlorophenylalanine.

25. The peptidomimetic compound according to claim 1, wherein X7 is Glu, Gln, Asp, Asn, Arg or Lys.

26. The peptidomimetic compound according to claim 1, wherein X8 is Trp or L-2-methyl-tryptophan.

27. The peptidomimetic compound according to claim 1, wherein X9 is Ser or Gln.

28. The peptidomimetic compound according to claim 1, wherein X10 is 4-aminobutanoic acid, beta-alanine, ((2R)-3-amino-2-(3-aminopropanoylamino) beta-alanine, Lys, L-ornithine, Cys or homocysteine.

29. A peptidomimetic compound having the sequence:

Cap1-X1-X2-X3-X4-X5-X6-X7-X8-Leu-X9-X10-Cap2 wherein:

Cap1 is an amino acid sequence comprising from 0-10 residues with a N-terminal blocking group;

X1 is any L or D-amino acid;

X2 is any L-amino acid;

X3 is an aliphatic L-amino acid with a molecular weight below 200 Da;

X4 is any L-amino acid;

X5 is Tyr or a L-tyrosine analog;

X6 is Phe or a L-phenylalanine analog;

X7 is any charged or neutral hydrophilic L-amino acid;

X8 is Trp or a L-tryptophan analog;

X9 is absent or any hydrophilic L-amino acid;

X10 is any L-amino acid; and

Cap2 is absent or carboxamide, and wherein the compound is capable of specifically binding to hemagglutinin (HA) of at least two influenza A virus strains comprising HA of two different subtypes from phylogenetic group 1.

30. A pharmaceutical composition comprising a peptidomimetic compound according to claim 1 and a pharmaceutically acceptable carrier or diluent.

31. A method of treating influenza in a subject in need thereof, the method comprising administering to the subject in need thereof a peptidomimetic compound according to claim 1.

32. A method of preventing influenza in a subject, the method comprising administering to the subject a peptidomimetic compound according to claim 1.

* * * * *

SEQUENCE LISTING

```
<160> NUMBER OF SEQ ID NOS: 9

<210> SEQ ID NO 1
<211> LENGTH: 11
<212> TYPE: PRT
<213> ORGANISM: Artificial Sequence
<220> FEATURE:
<223> OTHER INFORMATION: CP132070
<220> FEATURE:
<221> NAME/KEY: MISC_FEATURE
<222> LOCATION: (1)..(1)
<223> OTHER INFORMATION: Xaa is (S)-2-amino-5-phenylpentanoic acid,
      wherein Xaa is N-acetylated
<220> FEATURE:
<221> NAME/KEY: MISC_FEATURE
<222> LOCATION: (2)..(2)
```

```
<223> OTHER INFORMATION: Xaa is L-ornithine bound via an amide bond to
      Xaa at position 11
<220> FEATURE:
<221> NAME/KEY: MISC_FEATURE
<222> LOCATION: (11)..(11)
<223> OTHER INFORMATION: Xaa is beta-alanine bound via an amide bond to
      Xaa at position 2

<400> SEQUENCE: 1

Xaa Xaa Leu Arg Tyr Phe Glu Trp Leu Ser Xaa
1               5                   10


<210> SEQ ID NO 2
<211> LENGTH: 11
<212> TYPE: PRT
<213> ORGANISM: Artificial Sequence
<220> FEATURE:
<223> OTHER INFORMATION: CP141019
<220> FEATURE:
<221> NAME/KEY: misc_feature
<222> LOCATION: (1)..(1)
<223> OTHER INFORMATION: Xaa is (S)-2-amino-5-phenylpentanoic acid,
      wherein Xaa is N-acetylated
<220> FEATURE:
<221> NAME/KEY: misc_feature
<222> LOCATION: (2)..(2)
<223> OTHER INFORMATION: Xaa is L-ornithine bound via amide bond to Xaa
      at position 11
<220> FEATURE:
<221> NAME/KEY: misc_feature
<222> LOCATION: (6)..(6)
<223> OTHER INFORMATION: Xaa is L-3,4-dichlorophenylalanine
<220> FEATURE:
<221> NAME/KEY: misc_feature
<222> LOCATION: (11)..(11)
<223> OTHER INFORMATION: Xaa can be any naturally occurring amino acid,
      wherein Xaa is bound via an amide bond to Xaa at position 2

<400> SEQUENCE: 2

Xaa Xaa Leu Glu Tyr Xaa Glu Trp Leu Ser Xaa
1               5                   10


<210> SEQ ID NO 3
<211> LENGTH: 11
<212> TYPE: PRT
<213> ORGANISM: Artificial Sequence
<220> FEATURE:
<223> OTHER INFORMATION: CP141036
<220> FEATURE:
<221> NAME/KEY: MISC_FEATURE
<222> LOCATION: (1)..(1)
<223> OTHER INFORMATION: Xaa is (S)-2-amino-5-phenylpentanoic acid,
      wherein Xaa is N-acetylated
<220> FEATURE:
<221> NAME/KEY: MISC_FEATURE
<222> LOCATION: (2)..(2)
<223> OTHER INFORMATION: Xaa is L-ornithine bound via an amide bond to
      Xaa at position 11
<220> FEATURE:
<221> NAME/KEY: MISC_FEATURE
<222> LOCATION: (3)..(3)
<223> OTHER INFORMATION: Xaa is L-cyclopentylalanine
<220> FEATURE:
<221> NAME/KEY: MISC_FEATURE
<222> LOCATION: (11)..(1)
<223> OTHER INFORMATION: Xaa is beta-alanine bound via an amide bond to
      Xaa at position 2

<400> SEQUENCE: 3

Xaa Xaa Xaa Glu Tyr Phe Glu Trp Leu Ser Xaa
1               5                   10


<210> SEQ ID NO 4
```

```
<211> LENGTH: 11
<212> TYPE: PRT
<213> ORGANISM: Artificial Sequence
<220> FEATURE:
<223> OTHER INFORMATION: CP141037
<220> FEATURE:
<221> NAME/KEY: misc_feature
<222> LOCATION: (1)..(1)
<223> OTHER INFORMATION: Xaa is (S)-2-amino-5-phenylpentanoic acid,
      wherein Xaa is N-acetylated
<220> FEATURE:
<221> NAME/KEY: misc_feature
<222> LOCATION: (2)..(2)
<223> OTHER INFORMATION: Xaa is L-ornithine bound via an amide bond to
      Xaa at positon 11
<220> FEATURE:
<221> NAME/KEY: misc_feature
<222> LOCATION: (3)..(3)
<223> OTHER INFORMATION: Xaa is L-N-methyl-leucine
<220> FEATURE:
<221> NAME/KEY: misc_feature
<222> LOCATION: (11)..(11)
<223> OTHER INFORMATION: Xaa is beta-alanine bound via an amide bond to
      Xaa at position 2

<400> SEQUENCE: 4

Xaa Xaa Xaa Glu Tyr Phe Glu Trp Leu Ser Xaa
1               5                   10


<210> SEQ ID NO 5
<211> LENGTH: 11
<212> TYPE: PRT
<213> ORGANISM: Artificial Sequence
<220> FEATURE:
<223> OTHER INFORMATION: CP141066
<220> FEATURE:
<221> NAME/KEY: MISC_FEATURE
<222> LOCATION: (1)..(1)
<223> OTHER INFORMATION: Xaa is (S)-2-amino-5-phenylpentanoic acid,
      wherein Xaa is N-acetylated
<220> FEATURE:
<221> NAME/KEY: MISC_FEATURE
<222> LOCATION: (2)..(2)
<223> OTHER INFORMATION: Xaa is L-ornithine bound via amide bond to Xaa
      at position 11
<220> FEATURE:
<221> NAME/KEY: MISC_FEATURE
<222> LOCATION: (4)..(4)
<223> OTHER INFORMATION: Xaa is N6-(4-carboxybutanoyl)lysine
<220> FEATURE:
<221> NAME/KEY: MISC_FEATURE
<222> LOCATION: (11)..(11)
<223> OTHER INFORMATION: Xaa is beta-alanine bound via amide bond to Xaa
      at position 2

<400> SEQUENCE: 5

Xaa Xaa Leu Xaa Tyr Phe Glu Trp Leu Ser Xaa
1               5                   10


<210> SEQ ID NO 6
<211> LENGTH: 11
<212> TYPE: PRT
<213> ORGANISM: Artificial Sequence
<220> FEATURE:
<223> OTHER INFORMATION: CP141077
<220> FEATURE:
<221> NAME/KEY: MISC_FEATURE
<222> LOCATION: (1)..(1)
<223> OTHER INFORMATION: Xaa is (S)-2-amino-5-phenylpentanoic acid,
      wherein Xaa is N-acetylated
<220> FEATURE:
<221> NAME/KEY: MISC_FEATURE
<222> LOCATION: (2)..(2)
<223> OTHER INFORMATION: Xaa is L-ornithine bound via an amide bond to
      Xaa at position 11
```

-continued

<220> FEATURE:
<221> NAME/KEY: MISC_FEATURE
<222> LOCATION: (11)..(11)
<223> OTHER INFORMATION: Xaa is beta-alanine bound via an amide bond to
Xaa at position 2

<400> SEQUENCE: 6

Xaa Xaa Leu Glu Tyr Phe Glu Trp Leu Gln Xaa
1 5 10

<210> SEQ ID NO 7
<211> LENGTH: 11
<212> TYPE: PRT
<213> ORGANISM: Artificial Sequence
<220> FEATURE:
<223> OTHER INFORMATION: CP141100
<220> FEATURE:
<221> NAME/KEY: MISC_FEATURE
<222> LOCATION: (1)..(1)
<223> OTHER INFORMATION: Xaa is (S)-2-amino-5-phenylpentanoic acid,
wherein Xaa is N-acetylated
<220> FEATURE:
<221> NAME/KEY: MISC_FEATURE
<222> LOCATION: (2)..(2)
<223> OTHER INFORMATION: Xaa is L-ornithine bound via amide bond to Xaa
at position 11
<220> FEATURE:
<221> NAME/KEY: MISC_FEATURE
<222> LOCATION: (4)..(4)
<223> OTHER INFORMATION: Xaa is lysine bound via a chemical bridge to a
second cyclic peptide of SEQ ID NO:7
<220> FEATURE:
<221> NAME/KEY: MISC_FEATURE
<222> LOCATION: (11)..(11)
<223> OTHER INFORMATION: Xaa is beta-alanine bound via amide bond to Xaa
at position 2

<400> SEQUENCE: 7

Xaa Xaa Leu Xaa Tyr Phe Glu Trp Leu Ser Xaa
1 5 10

<210> SEQ ID NO 8
<211> LENGTH: 11
<212> TYPE: PRT
<213> ORGANISM: Artificial Sequence
<220> FEATURE:
<223> OTHER INFORMATION: CP141099
<220> FEATURE:
<221> NAME/KEY: MISC_FEATURE
<222> LOCATION: (1)..(1)
<223> OTHER INFORMATION: Xaa is (S)-2-amino-5-phenylpentanoic acid,
wherein Xaa is N-acetylated
<220> FEATURE:
<221> NAME/KEY: MISC_FEATURE
<222> LOCATION: (2)..(2)
<223> OTHER INFORMATION: Xaa is L-ornithine bound via amide bond to Xaa
at position 11
<220> FEATURE:
<221> NAME/KEY: MISC_FEATURE
<222> LOCATION: (11)..(11)
<223> OTHER INFORMATION: Xaa is ((2R)-3-amino-2-(3-aminopropanoylamino)
beta-alanine bound via amide bond to Xaa at position 2

<400> SEQUENCE: 8

Xaa Xaa Leu Glu Tyr Phe Glu Trp Leu Ser Xaa
1 5 10

<210> SEQ ID NO 9
<211> LENGTH: 11
<212> TYPE: PRT
<213> ORGANISM: Artificial Sequence
<220> FEATURE:
<223> OTHER INFORMATION: CP141032

-continued

```
<220> FEATURE:
<221> NAME/KEY: MISC_FEATURE
<222> LOCATION: (1)..(1)
<223> OTHER INFORMATION: Arg is N-acetylated
<220> FEATURE:
<221> NAME/KEY: MISC_FEATURE
<222> LOCATION: (2)..(2)
<223> OTHER INFORMATION: Xaa is L-ornithine, which is linked via TSAT
      linkage to Xaa at positions 4 and 11
<220> FEATURE:
<221> NAME/KEY: MISC_FEATURE
<222> LOCATION: (4)..(4)
<223> OTHER INFORMATION: Xaa is L-ornithine, which is linked via TSAT
      linkage to Xaa at positions 2 and 11
<220> FEATURE:
<221> NAME/KEY: MISC_FEATURE
<222> LOCATION: (11)..(11)
<223> OTHER INFORMATION: Xaa is L-ornithine, which is linked via TSAT
      linkage to Xaa at positions 2 and 4

<400> SEQUENCE: 9

Arg Xaa Leu Xaa Tyr Phe Glu Trp Leu Ser Xaa
1               5                   10
```